US008869297B2

(12) United States Patent
Hanov et al.

(10) Patent No.: US 8,869,297 B2
(45) Date of Patent: Oct. 21, 2014

(54) EFFECTUATING CLINICAL ORDERS UPON RECEIPT OF AUTHORIZATION FROM TWO PRIVILEGED CLINICIANS

(75) Inventors: Yegor Faridovich Hanov, Overland Pask, KS (US); Kim Ince, Raymore, MO (US); Lisa Pastine, Shawnee, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 667 days.

(21) Appl. No.: 12/684,709

(22) Filed: Jan. 8, 2010

(65) Prior Publication Data

US 2011/0173704 A1    Jul. 14, 2011

(51) Int. Cl.
*H04L 29/06* (2006.01)
*G06Q 50/22* (2012.01)
*G06Q 10/06* (2012.01)
*G06F 19/00* (2011.01)

(52) U.S. Cl.
CPC ............ *H04L 63/08* (2013.01); *G06F 19/3456* (2013.01); *G06F 19/34* (2013.01); *G06Q 50/22* (2013.01); *G06F 19/327* (2013.01); *G06Q 10/06* (2013.01)
USPC .............................................. 726/27; 705/2

(58) Field of Classification Search
CPC .. G06F 19/34; G06F 19/3418; G06F 19/3456
USPC ..................................... 726/2, 26–28; 705/2–3
See application file for complete search history.

(56) References Cited

U.S. PATENT DOCUMENTS

| 6,876,977 | B1* | 4/2005 | Marks ........................ 705/26.62 |
| 7,774,213 | B2* | 8/2010 | Alexander et al. ................. 705/2 |
| 2002/0133379 | A1* | 9/2002 | Lewis et al. ....................... 705/4 |
| 2003/0208477 | A1* | 11/2003 | Smirniotopoulos et al. ...... 707/3 |
| 2005/0281601 | A1* | 12/2005 | Papetti ..................... 400/124.01 |
| 2006/0129433 | A1* | 6/2006 | Koneru ............................. 705/3 |
| 2008/0046286 | A1* | 2/2008 | Halsted ............................ 705/2 |
| 2010/0082548 | A1* | 4/2010 | Crockett et al. .............. 707/662 |
| 2011/0166884 | A1* | 7/2011 | Lesselroth et al. ................ 705/3 |

* cited by examiner

*Primary Examiner* — Hadi Armouche
*Assistant Examiner* — Dao Ho
(74) *Attorney, Agent, or Firm* — Shook, Hardy & Bacon L.L.P.

(57) ABSTRACT

Computerized methods and systems methods and systems in a clinical computing environment for effectuating clinical orders only upon receipt of an authorization from at least two privileged clinicians, i.e., two clinicians having appropriate ordering privileges, are provided. Upon receipt of an order from a privileged clinician that requires authorization by at least two privileged clinicians, such order is assigned a non-effectuated status until such time as the required review by one or more other privileged clinicians is completed. While in the non-effectuated status, the order is not exposed to clinicians or others that do not have appropriate ordering privileges to prescribe and/or authorize the order.

15 Claims, 13 Drawing Sheets

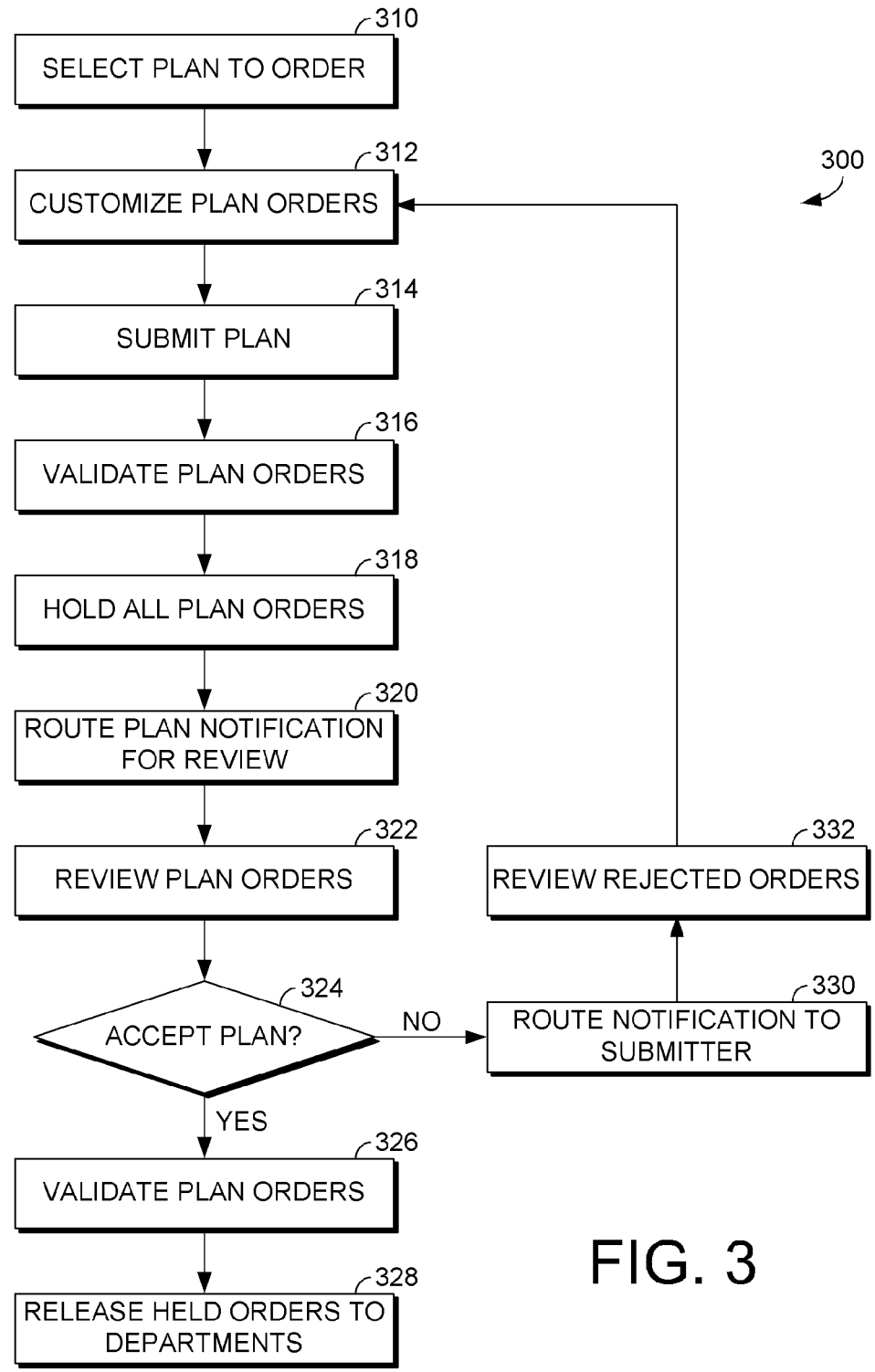

DOE, JOHN – ADD PLAN

ARST 0431 IFOSFAMIDE/ETOPOSIDE

― SELECT VISIT AND START TIME ―

○ THIS VISIT
○ FUTURE INPATIENT VISIT
● FUTURE OUTPATIENT VISIT

ESTIMATED START DATE OF PLAN?
○ IN ☐ DAY(S)
○ IN ☐ WEEK(S)
● IN ☐1☐ MONTH(S)
EST. START ☐08/13/2009☐ ☐0800☐

― CONFIRM PHASE ACTION ―

| PHASE | START DATE/TIME | ACTION |
|---|---|---|
| PRETREATMENT MONITORING | 8/13/2009 8:00 AM | ORDER NOW |
| SCHEDULED CHEMO VISIT | 8/13/2009 8:00 AM | ORDER NOW |
| CHEMOTHERAPY | *EST. 8/13/2009 8:00 AM | ORDER FOR FUTURE VISIT |

― ADDITIONAL REVIEW SETTINGS ―

☑ REVIEW REQUIRED
REVIEW PROVIDER
☐ SMITH MD, JANE ☐

[ OK ]  [ CANCEL ]

DOE, JOHN

INBOX SUMMARY

| INBOX | PROXIES | POOLS |

☐ PRIORITY ITEMS (1)
  ☐ MESSAGES (1)
    RENEWAL REQUESTS (1)

☐ INBOX ITEMS (20)
  ☐ RESULTS (10)
    ABNORMAL (1)
    NORMAL (1)
  ☐ DOCUMENTS (1)
    DOCUMENTS TO SIGN
  ☐ MESSAGES (5)
    GENERAL MESSAGES (2)
    RENEWAL REQUESTS (2)
    MESSAGES FROM PATIENTS (1)
    CC MESSAGES
  ☐ ORDERS (5)
    PROTOCOL REVIEW ORDERS (5)

☐ WORK ITEMS (0)

☐ NOTIFY RECEIPTS (35)
  NOTIFY RECEIPTS (35)
  SENT ITEMS
  MESSAGING TRASH CAN

| PROTOCOL ORDERS |

⚙ COMMUNICATE ▼ | 📂 OPEN | 📰 MESSAGE JOURNAL | ✏ FORWARD ONLY | 👤 SELECT PATIENT | ⋮ SELECT ALL

| PATIENT NAME | CREATION DATE/TIME | PLAN NAME | FROM | ORDER ACTION |
|---|---|---|---|---|
| THOMPSON, ANGELA | 05/09/2009 12:30 | CMF CYCLE 1 | HOMES, JUDY | ORDER |
| MCGUIRE, SALLY | 05/09/2009 12:00 | CMF CYCLE 1 | BROWN, ERIC MD | ORDER |
| SMITH, SALLY | 05/09/2009 08:17 | ARST0431 IFOSFAMIDE, ETOPOSIDE | BROWN, ERIC MD | ORDER |
| RICHARDS, KATHY | 05/08/2009 09:30 | CMF CYCLE 1 | BLODGETT, TIM MD | ORDER |
| JONES, VICTOR | 05/08/2009 07:45 | CMF CYCLE 1 | GREER, KIM | ORDER |

INBOX SUMMARY

| INBOX | PROXIES | POOLS |

- ⊞ PRIORITY ITEMS (0)
- ⊟ INBOX ITEMS (20)
  - ⊟ RESULTS (10)
    - ABNORMAL (1)
    - NORMAL (9)
  - ⊟ DOCUMENTS (1)
    - DOCUMENTS TO SIGN
  - ⊟ MESSAGES (5)
    - GENERAL MESSAGES (2)
    - RENEWAL REQUESTS (2)
    - MESSAGES FROM PATIENT (1)
    - CC MESSAGES
  - ⊟ ORDERS (5)
    - *PROTOCOL REVIEW ORDERS (5)*
- ⊞ WORK ITEMS (0)
- ⊟ NOTIFY RECEIPTS (35)
  - NOTIFY RECEIPTS (35)
  - SENT ITEMS
  - MESSAGING TRASH CAN

---

| PROTOCOL ORDERS | ORDER PROPOSAL: DOE, JOHN ✕ |

✎ FORWARD ONLY  ✉ SEND REMINDER  ⇅ SEND TO CONSUMER | 🖨 PRINT  ⇧ ⇩

DOE, JOHN 6Y M   ALLERGIES: NKA   VISIT REASON: CHEMOTHERAPY   IQHEALTH: YES
DOB: 10/10/2003  MRN: 00-00-0989  FIN: 005436  LOCATION: BW8E; 8E 05; 0  VISIT DATE: 05/09/2009  HEIGHT: 155 CM   WEIGHT: 45 KG   BSA: 1.39 M2   PCP: JOHN JONES, MD

DISPLAY: ALL ▸   ✎ MODIFY   📋 ORDER INFORMATION

| OFFSET | COMPONENT | STATUS | DETAILS |
|---|---|---|---|
| ARST0431 IFOSFAMIDE, ETOPOSIDE, CHEMOTHERAPY (INITIATED – PENDING REVIEW) START DATE/TIME: 05/08/2009 8:00 AM | | | |
| ORDERED BY: 01/15/2009 1:25 PM BY JONES, JOHN MD | | | |
| ☑ 0HR | 📋 ETOPOSIDE | *PENDING REVIEW | 10 MG/M2, IV, ONCE, ROUTINE, DAY 1-5 |
| | CALCULATED DOSE: 139 MG | TARGET DOSE: 100 MG/M2 | ROUTE: IV |
| ☑ +1HR | 📋 IFOSFAMIDE WITH MESNA | *PENDING REVIEW | 10 MG/M2, IV, ONCE, ROUTINE, DAY 1-5 |
| | IFOSFAMIDE: CALCULATED DOSE: 2500 MG | TARGET DOSE: 1800 MG/M2 | ROUTE: IV |
| | MESNA: CALCULATED DOSE: 500 MG | TARGET DOSE: 360 MG/M2 | ROUTE: IV |
| ☑ +5HR | 📋 MESNA | *PENDING REVIEW | 5MCG/KG, IV, Q4H, 2 DOSES, ROUTINE, DAY 1-5 |
| | CALCULATED DOSE: 225 MCG | TARGET DOSE: 5 MG/M2 | ROUTE: IV    WEIGHT: 47 KG |
| ☑ | 📋 URINE HEME ORDER | *PENDING REVIEW | URINE, LAB COLLECT, ROUTINE, DAY 2,5 |

| COMPONENT | STATUS | DETAILS |
|---|---|---|
| (ONC TEST, CHEMOTHERAPY (INITIATED) LAST UPDATED ON: 12/15/2008 12:58 PM BY: INCE, KIM) | | 12/15/2008 12:00 PM – PHASE END |
| -2 HR  WHITE BLOOD CELL – LESS THAN 4,000 CM3 | ORDERED | 1,000 ML/MIN, IV ROUTINE, 12/15/2008 12:00 PM, 6 HR, PHYSICIAN STOP, STOP DATE 12/15/2008 5:59 PM |
|   DEXTROSE 5% IN WATER 1,000 ML/MIN | ACTIVATED | |
|  SPECIFIC GRAVITY URIN – 1.015 OR 1.010 OR <= 1.00 | ACTIVATED | BY 12/15/2008 2:00 PM |
| 0 HR  ETOPOSIDE | ORDERED | 139 MG, IV, START DATE 12/15/2008 2:00 PM, STOP DATE 12/15/2008 2:00 PM, ONCE ONLY TARGET DOSE: ETOPOSIDE 100 MG/M2 12/12/2008 12:46:48 PM |
| +2 HR  IFOSFAMIDE WITH MESNA | ORDERED | IV, T: N, 1 HR, PHYSICIAN STOP |
| +5 HR  MESNA | ORDERED | 225 MCG, IV, START DATE 12/15/2008 7:00 PM, Q4H – R15 TARGET DOSE: MESNA 5 MCG/KG 12/12/2008 12:47:05 PM |
|   FILGRASTIM | ORDERED | 225 MCG, IV, 16 DAY(S) PRINT REQUISITION TARGET DOSE: FILGRASTIM 5 MCG/KG 12/12/2008 12:47:16 PM |
|  URINE DIPSTICK | ORDERED | 12/15/2008 12:00 PM |

510

512

PLAN REJECT

*REJECT REASON:
DUPLICATE PLAN ▶

*FREETEXT REASON:
THESE ORDERS NEED TO BE REVIEWED FOR CLINICAL RELEVANCE.

SELECT THE COMPONENT(S) THAT NEED TO BE ADDRESSED PRIOR TO APPROVAL:

| | COMPONENT | STATUS | ORDER DETAILS |
|---|---|---|---|
| DIET | | | |
| ☐ | ☑ NPO | REVIEW REQUIRED | EXCEPT ICE, 1/8/2010 3:56 PM, PRN |
| LABORATORY | | | |
| ☑ | ☑ GLUCOSE, FASTING | REVIEW REQUIRED | BLOOD, STAT COLLECT, 1/8/2010 3:56 PM |
| DIAGNOSTIC TESTS | | | |
| ☑ | ☑ XR CHEST 2V | REVIEW REQUIRED | 1/8/2010 3:56 PM, RAD TYPE, ADULT |

DOE, JOHN - 329832

[OK] [CANCEL]

PLAN INFORMATION

LP MULTIPHASE PLAN – WEEK 20 OF 20 (VERSION 1)
- LP PHASE 1 (SYSTEM ID 72262076)
  - ORDER (PLANNED) – 1/8/2010 1:56 PM – PASTINE, LISA
- LP PHASE 2 (SYSTEM ID 72262077)
  - REJECT REVIEW (INITIATED – REJECTED) – 1/8/2010 2:02 PM – POWERPLAN, MD CNA
    - REASON: DUPLICATE PLAN, THESE ORDERS NEED TO BE REVIEWED FOR CLINICAL RELEVANCE.
  - MODIFY (INITIATED – REVIEW REQUIRED) – 1/8/2010 2:02 PM – POWERPLAN, MD CNA
  - ROUTE FOR REVIEW (INITIATED – REVIEW REQUIRED) – 1/8/2010 1:56 PM – PASTINE, LISA
  - ORDER (INITIATED) – 1/8/2010 1:56 PM – PASTINE, LISA

CLINICAL TRIAL/STUDY

FIG. 13

EFFECTUATING CLINICAL ORDERS UPON RECEIPT OF AUTHORIZATION FROM TWO PRIVILEGED CLINICIANS

BACKGROUND

Orders for high risk medications, such as chemotherapy medications, often require a second signature or authorization by an attending physician or other clinician having ordering privileges (i.e., a privileged clinician) prior to those orders being effectuated, that is, dispatched to the pharmacy. In some instances, the requirement for the additional privileged clinician's authorization is a state-mandated regulation. While current electronic clinical ordering systems support requiring a privileged clinician's review of orders entered by non-privileged clinicians (that is, clinicians without ordering privileges), if orders are input by a clinician having appropriate ordering privileges, such orders are effectuated without requiring review and acceptance by a second privileged clinician.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter Embodiments of the present invention relate to methods and systems in a clinical computing environment for effectuating clinical orders only upon receipt of an authorization from at least two privileged clinicians, that is, two clinicians having appropriate ordering privileges. As utilized herein, a "clinician" may be, but is not limited to, a treating physician; a specialist such as a surgeon, a radiologist, a cardiologist, or an oncologist; a mid-level provider; a resident; a fellow; an emergency medical technician; a physicians' assistant; a nurse practitioner; a nurse; a nurses' aide; a pharmacist; a dietician; a microbiologist; a laboratory expert; a laboratory technologist; a genetic counselor; a researcher; a veterinarian; a student; and the like. In accordance with embodiments hereof, upon receipt of an order from a privileged clinician that requires authorization by at least two privileged clinicians (such requirement being state-mandated, facility-required, regulation-mandated, or the like), such order is assigned a non-effectuated status until such time as the required review by one or more other privileged clinicians (i.e., a privileged clinician other than the privileged clinician from whom the order was received) is completed. While in the non-effectuated status, the order is not exposed to clinicians or others that do not have appropriate ordering privileges to prescribe and/or authorize the order.

Accordingly, in one embodiment, the present invention is directed to one or more computer-readable storage media having computer-executable instructions embodied thereon that, when executed, perform a method for effectuating clinical orders only upon receipt of an authorization from a first privileged clinician and a second privileged clinician. The method includes receiving an order from the first privileged clinician, the received order including all order details necessary to effectuate the order; providing a notification to the second privileged clinician, the notification indicating that review of the order by the second privileged clinician is required before the order can be effectuated; receiving an order acceptance indication from the second privileged clinician; and, upon receipt of the order acceptance indication, effectuating the order.

In another embodiment, the present invention is directed to one or more computer-readable storage media having computer-executable instructions embodied thereon that, when executed, perform a method for effectuating clinical orders only upon receipt of an authorization from a first privileged clinician and a second privileged clinician. The method includes receiving an order from the first privileged clinician, the received order including all order details necessary to effectuate the order and requiring action by a third clinician other than the first and the second clinicians. The method further includes determining that the order requires authorization from the second privileged clinician to be effectuated and assigning the order a non-effectuated status pending receipt of the authorization from the second privileged clinician. The non-effectuated status prevents exposure of the order to the third clinician. Still further, the method includes providing a notification to the second privileged clinician, the notification indicating that authorization of the order by the second privileged clinician is required before the order can be effectuated; and providing the second privileged clinician with options to accept the order as received, reject the order, or accept a modified version of the order. Upon receiving an order acceptance indication from the second privileged clinician, the order is assigned an effectuated status that permits exposure of the order to the third clinician.

In yet another embodiment, the present invention is directed to one or more computer-readable storage media having computer-executable instructions embodied thereon that, when executed, cause presentation of a user interface. The user interface includes an orders display area that presents one or more orders that have been received for a particular patient from a first privileged clinician; and an order status display area that presents a status indicator for each of the one or more orders. At least one of the status indicators indicates that review of an associated order is required by a second privileged clinician before the associated order can be effectuated. Upon receipt of an acceptance indicator from the second privileged clinician, the at least one of the status indicators changes to indicate that the associated order is effectuated.

BRIEF DESCRIPTION OF THE DRAWINGS

The present invention is described in detail below with reference to the attached drawing figures, wherein:

FIG. 3 is a flow diagram showing a method for effectuating a healthcare plan including a plurality of clinical orders only upon receipt of an authorization from a first privileged clinician and a second privileged clinician with regard to at least one of the plurality of orders, in accordance with an embodiment of the present invention;

FIG. 4 is a screen display of an exemplary user interface for use, for instance, by a first privileged clinician, in inputting a clinical order requiring review by a second privileged clinician to be effectuated, in accordance with an embodiment of the present invention;

FIG. 5 is a screen display of an exemplary user interface illustrating orders that have been input by a first privileged clinician and require authorization by a second privileged clinician to be effectuated, such orders having a "Review Required" status, in accordance with an embodiment of the present invention;

FIG. 6 is a screen display of an exemplary user interface illustrating a message center for notifying a second privileged clinician of orders requiring his or her review and authorization, in accordance with an embodiment of the present invention;

FIG. 7 is a screen display of an exemplary user interface illustrating detailed information with respect to orders requiring review that may be displayed upon selection of a particular patient name in the message center of FIG. 6, in accordance with an embodiment of the present invention;

FIG. 8 is a screen display of an exemplary user interface illustrating orders that have been input by a first privileged clinician and received authorization by a second privileged clinician, such orders having an "Ordered" status, in accordance with an embodiment of the present invention;

FIG. 11 is a screen display of an exemplary user interface illustrating that a second privileged clinician may identify which order(s) among a plurality of orders related to one another as part of a healthcare plan or phase of a healthcare plan caused the second privileged clinician to reject the plan or phase and provide a reason for the rejection, in accordance with an embodiment of the present invention;

FIG. 13 is a screen display of an exemplary user interface illustrating that, once a second privileged clinician has rejected an order, the reason for the rejection may be displayed in association with the healthcare plan information, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide methods and systems in a clinical computing environment for effectuating clinical orders only upon receipt of an authorization from at least two privileged clinicians, that is, two clinicians having appropriate ordering privileges. Upon receipt of an order from a privileged clinician that requires authorization by at least two privileged clinicians (such requirement being state-mandated, facility-required, regulation-mandated, or the like), such order is assigned a non-effectuated status until such time as the required review by one or more other privileged clinicians (i.e., a privileged clinician other than the privileged clinician from whom the order was received) is completed. While in the non-effectuated status, the order is not exposed to clinicians or others that do not have appropriate ordering privileges to prescribe and/or authorize the order. An exemplary operating environment for embodiments of the present invention is described below.

Figure 1:
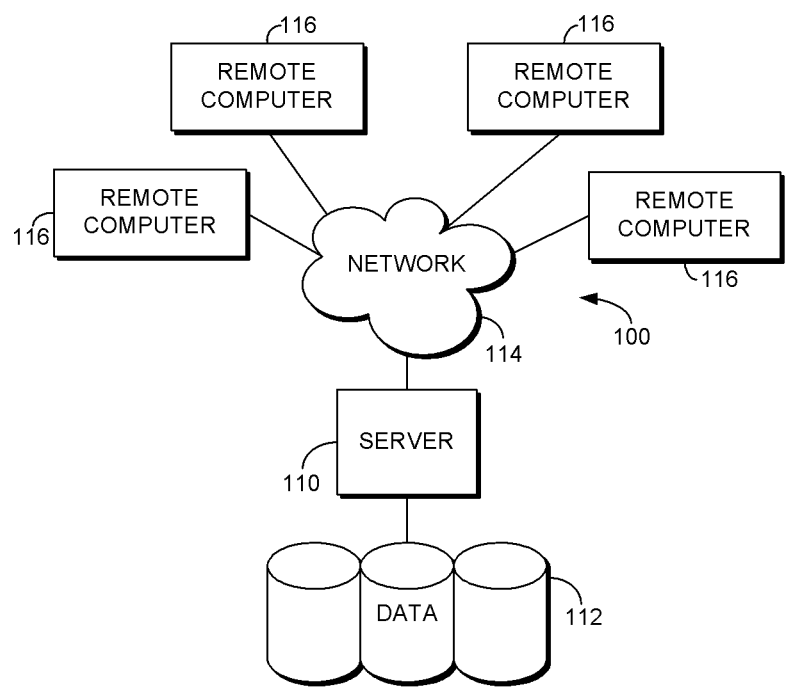
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of embodiments of the invention. Neither should the medical information computing system environment 100 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 110. Components of the server 110 may include, without limitation, a processing unit, internal system memory, and a suitable system bus for coupling various system components, including the database cluster 112, with the server 110. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 110 typically includes, or has access to, a variety of computer-readable media, for instance, the database cluster 112. Computer-readable media can be any available media that may be accessed by the server 110, and includes volatile and nonvolatile media, as well as removable and non-removable media. By way of example, and not limitation, computer readable media may comprise computer-readable storage media. Computer-readable storage media may include, without limitation, volatile and nonvolatile media, as well as removable and non-removable media implemented in any method or technology for storage of information, such as computer-readable instructions, data structures, program modules, or other data. In this regard, computer-readable storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 110. Combinations of any of the above also may be included within the scope of computer-readable media.

The computer-readable storage media discussed above and illustrated in FIG. 1, including database cluster 112, provide storage of computer-readable instructions, data structures, program modules, and other data for the server 110.

The server 110 may operate in a computer network 114 using logical connections to one or more remote computers 116. The remote computers 116 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians; specialists such as surgeons, radiologists, cardiologists, and oncologists; mid-level providers; residents; fellows; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 116 may also be physically located in non-traditional medical care environments so that the entire health care community may be capable of integration on the network. The remote computers 116 may be personal computers, servers, routers, network PCs, peer devices, other common network nodes, or the like, and may include some or all of the elements described above in relation to the server 110. The devices can be personal digital assistants or other like devices.

Exemplary computer networks 114 may include, without limitation, local area networks (LANs) and/or wide area networks (WANs). Such networking environments are commonplace in offices, enterprise-wide computer networks, intranets, and the Internet. When utilized in a WAN networking environment, the server 110 may include a modem or other means for establishing communications over the WAN, such as the Internet. In a networked environment, program modules or portions thereof may be stored in the server 110, in the database cluster 112, or on any of the remote computers 116. For example, and not by way of limitation, various application programs may reside on the memory associated with any one or more of the remote computers 116. It will be appreciated by those of ordinary skill in the art that the network connections shown are exemplary and other means of establishing a communications link between the computers (e.g., the server 110 and one or more of the remote computers 116) may be utilized.

In operation, a user may enter commands and information into the server 110 or convey the commands and information to the server 110 via one or more of the remote computers 116 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 110. In addition to a monitor, the server 110 and/or remote computers 116 may include other peripheral output devices, such as speakers and a printer.

Although many other internal components of the server 110 and the remote computers 116 are not shown, those of ordinary skill in the art will appreciate that such components and their interconnection are well known. Accordingly, additional details concerning the internal construction of the server 110 and the remote computers 116 are not further disclosed herein.

Although methods and systems of embodiments of the present invention are described as being implemented in a WINDOWS operating system, operating in conjunction with an Internet-based system, one of ordinary skill in the art will recognize that the described methods can be implemented in any system supporting the required authorization of two or more privileged clinicians before an order can be effectuated. In particular, the described methods can be implemented in any system supporting the receipt of orders from privileged clinicians and the assigning of a non-effectuated status to such orders until authorization from a second privileged clinician is received. As contemplated by the language above, the methods of embodiments of the present invention may also be implemented on a stand-alone desktop, personal computer, or any other computing device used in a healthcare environment, home-computing environment, or any of a number of other locations.

Figure 2:
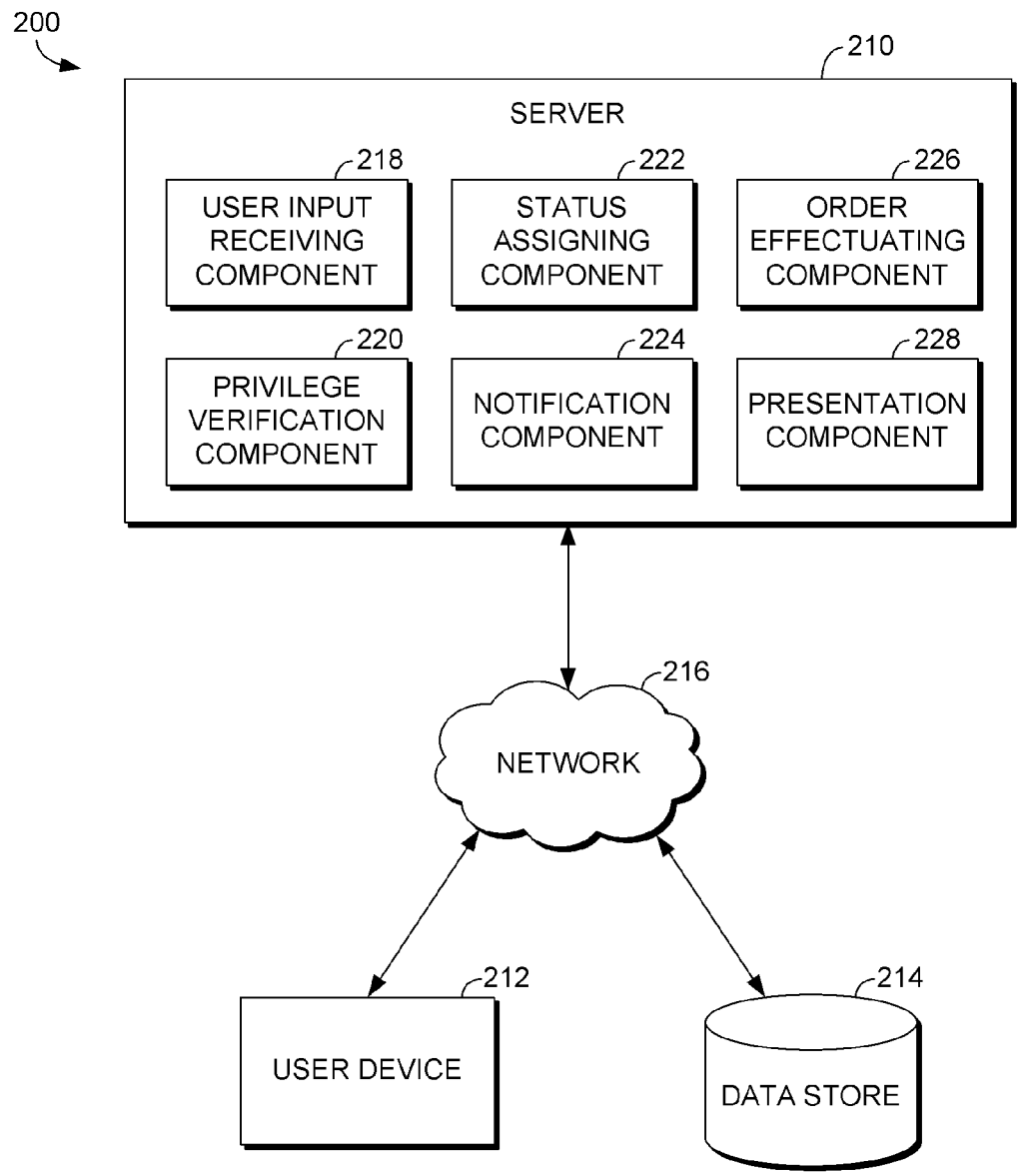
FIG. 2 is a block diagram of an exemplary computing system in which embodiments of the invention may be employed.

As previously mentioned, embodiments of the present invention relate to methods and systems in a clinical computing environment for effectuating clinical orders only upon receipt of an authorization from at least two privileged clinicians, that is, two clinicians having appropriate ordering privileges with respect to the subject clinical order. With reference to FIG. 2, an exemplary computing system suitable for implementing embodiments of the present invention is illustrated and designated generally as reference numeral 200. The system 200 includes a server 210, a user device 212, and a data store 214, all in communication with one another through a network 216. The network 216 may include, without limitation, one or more local area networks (LANs) and/or wide area networks (WANs). Such networking environments are commonplace in offices, enterprise-wide computer networks, intranets, and the Internet. Accordingly, the network 216 is not further described herein.

The data store 214 is configured to store information, for instance, associated with a plurality of patients' electronic medical records (EMRs). (The terms "individual," "person," and "patient" are used interchangeably herein and are not meant to limit the nature of the referenced individual in any way. Rather the methods and systems described herein are equally applicable, for instance, in a veterinary setting. Further, use of the term "patient" is not meant to imply any particular relationship between the individual and those inputting and/or authorizing orders for the individual.) The data store 214 is further configured to store information, for instance, associated with a plurality of clinicians and their associated ordering privileges. Such information may include, without limitation, an identity of each of the plurality of clinicians, a title and/or position that each of the plurality of clinicians holds, ordering privileges associated with each of the plurality of clinicians, ordering privileges associated with subsets of the plurality of clinicians (for instance, based upon title or position), any clinician groups to which each of the plurality of clinicians belongs that may be relevant to the clinician's ordering privileges, and the like. In embodiments, the data store 214 is configured to be searchable for one or more clinicians, ordering privileges associated with a clinician, ordering privileges associated with groupings of clinicians, and the like. It will be understood and appreciated by those of ordinary skill in the art that the information stored in the data store 214 may be configurable and may include any information relevant to patients' EMRs, clinicians and their respective ordering privileges, and the like. The content and volume of such information are not intended to limit the scope of embodiments of the present invention in any way. Further, though illustrated as a single, independent component, the data store 214 may, in fact, be a plurality of data stores, for instance, a database cluster (e.g., the database cluster 112 of FIG. 1), portions of which may reside on the server 210, the user device 212, another external computing device (not shown) and/or any combination thereof.

The server 210 includes various components and is configured to operate utilizing at least a portion of the information stored in the data store 214. The illustrated server 210 includes a user input receiving component 218, a privilege verification component 220, a status assigning component 222, a notification component 224, an order effectuating component 226, and a presentation component 228. It will be understood and appreciated by those of ordinary skill in the art that other components not shown may also be included with the system 200. Further, additional components not shown may also be included within any of the server 210, the user device 212, the data store 214, and/or another external computing device (not shown). Any and all such variations are contemplated to be within the scope of embodiments hereof.

The user input receiving component 218 is configured for receiving input of information related to clinical orders. In particular, the user input receiving component 218 is configured for receiving input regarding clinical orders placed by privileged clinicians, that is, clinicians having all appropriate ordering privileges as they relate to the order in question. In this regard, the user input receiving component 218 is configured to receive a plurality of clinical orders placed by a first privileged clinician, at least a portion of the plurality of clinical orders requiring review and authorization or verification by a second privileged clinician. The received clinical orders include all order details necessary to effectuate the order. That is, the received clinical orders include sufficient order information such that, absent a requirement that the order be reviewed and authorized by a second privileged clinician, the orders would be capable of being effectuated in their received state. Accordingly, any and all appropriate clinical alerts deemed necessary with respect to the subject order, have been provided and reviewed by the first privileged clinician upon the clinical order being received by the user input receiving component 218. Additionally, a received order may be a reference order or an order that differs from a reference order in that it includes at least one customization specific to the associated patient. As such, all necessary patient-specific customizations have been provided at the direction of the first privileged clinician upon the clinical order being received by the user input receiving component. Input of the clinical order at the direction of the first privileged clinician evidences the first privileged clinician's authorization of the subject order.

The user input receiving component 218 is further configured to receive input from a second privileged clinician, that is, a clinician other than the first privileged clinician (ordering clinician) that has all appropriate ordering privileges as they relate to the order in question. In this regard, the user input receiving component 218 is configured to receive order acceptance indications from the second privileged clinician, that is, indications that the second privileged clinician has reviewed and accepted, authorized and/or verified the subject order. As more fully described below, upon reviewing an order requiring review and authorization, the second privileged clinician may elect to accept the order as received, to modify the order and authorize the modified version of the order, or to reject the order. As such, the user input receiving component 218 is additionally configured to receive modifications to a reviewed order at the direction of the second privileged clinician and to receive order rejection notifications as well. Receipt of an order acceptance indication (whether related to the order as received or in a modified state) evidences the second privileged clinician's authorization of the subject order.

Clinical orders are requests placed by healthcare providers or clinicians for, e.g., procedures, medications, laboratory tests, evaluations, treatments, and nursing tasks to be done for a patient. A healthcare plan includes multiple orders for treatment for a particular problem or ailment. For example, a healthcare plan for a cancer patient may include multiple medication orders, laboratory testing orders and orders for diagnostic tests. Often times, an order (or set of orders) will set forth a healthcare plan having components which span multiple phases. For instance, a healthcare plan for a chemotherapy protocol may specify that a particular medication is to be given in a specified dosage on three separate days, e.g., Day 1, Day 8, and Day 15. In this instance, each day may be viewed as a separate phase. Phases, however, are not limited to units of time. In simple terms, a phase is merely a plan within a plan and, accordingly, may be a unit of time, a diagnostic grouping, or any other sub-plan within a healthcare plan. In accordance with embodiments hereof, the user input receiving component 218 is configured to receive clinical orders individually and to receive a plurality of orders, each of the plurality of orders being associated with one another as part of a healthcare plan or a phase of a healthcare plan.

The privilege verification component 220 is configured for determining whether or not a received order requires review, authorization and/or verification of a second privileged clinician in order to be effectuated. In the event that a plurality of orders is received, the orders being associated with one another as part of a healthcare plan or a phase of a healthcare plan, the privilege verification component 220 is configured for determining whether any of the orders of the plurality requires review, authorization and/or verification of a second privileged clinician in order to be effectuated. The privilege verification component 220 is further configured for determining whether a clinician placing or reviewing an order has the appropriate ordering privileges as they relate to the subject order. In this regard, the privilege verification component 220 communicates with the data store 214 through the network 216.

The status assigning component 222 is configured for assigning one of a plurality of statuses to a received order. If a received order is determined (e.g., by the privilege verification component 220) to require review, authorization and/or verification from a second privileged clinician in order to be effectuated, the status assigning component 222 is configured to assign the received order a non-effectuated (or "pending review") status pending receipt of the required authorization from a second privileged clinician. The non-effectuated (or "pending review") status prevents exposure of the order to departments and clinicians other than those either placing the subject order or having all appropriate ordering privileges to authorize the order. For instance, if a received order is for a chemotherapy medication to be administered to a patient and a state-regulation requires a second privileged clinician's authorization for the medication to be administered, the order will be in a non-effectuated state and will not be dispatched to the pharmacy until the second privileged clinician's authorization has been received (assuming the pharmacist does not have appropriate ordering privileges to effectuate the subject order).

In the event that a plurality of orders is received, the orders being associated with one another as part of a healthcare plan or a phase of a healthcare plan, if any of the plurality of orders is determined to require review, authorization and/or verification from a second privileged clinician in order to be effectuated, the status assigning component 222 is configured to assign each of the plurality of orders a non-effectuated status. As such, none of the plurality of orders comprising the healthcare plan or phase of the healthcare plan will be exposed to departments or clinicians other than those clinicians placing the subject order or having all appropriate ordering privileges to authorize the order until all of the orders in the plurality are assigned an "effectuated" status, as more fully described below.

If a received order is determined (e.g., by the privilege verification component) to not require review, authorization and/or verification from a second privileged clinician in order to be effectuated, or upon receipt of any required authorization by a second privileged clinician (e.g., by the user input receiving component 218), the status assigning component 222 is configured to assign the received order an effectuated (or "ordered") status. The effectuated (or "ordered") status permits exposure of the order to persons and departments other than the first and second privileged clinicians from whom action may be required with regard to the order.

The notification component 224 is configured for generating notifications directed to one or more privileged clinicians (other than the ordering privileged clinician), the notification indicating that review of the subject order by the second privileged clinician is required before the subject order can be effectuated. In the event a second privileged clinician rejects an order upon review, the notification component 224 is further configured for generating a notification directed to the ordering privileged clinician, the notification indicating that the subject order has been rejected.

Upon receipt of an order acceptance indication, or upon the privilege verification component 220 determining that review and authorization of a received order is not required, the order effectuating component 226 is configured to effectuate the order. That is, the order effectuating component 226 is configured for exposing and dispatching the subject order to those persons and/or departments from whom action may be required with regard to the order. In the event that a plurality of orders associated with one another as part of a healthcare plan or a phase of a healthcare plan was received, and any of the plurality of orders was determined to require review, authorization and/or verification from a second privileged clinician in order to be effectuated, the order effectuating component 226 is configured for exposing each of the plurality of orders to those persons and/or departments from whom action may be required with regard to any of the plurality of orders upon receipt of an order acceptance indication for all orders of the plurality for which review was determined to be required.

The presentation component 228 is configured to cause clinical orders, associated order details, notifications and the like to be displayed in association with a screen display of the user device 212. For instance, the presentation component 228 is configured to cause display of one or more of the exemplary user interfaces shown in FIGS. 4-8.

Turning now to FIG. 3, a flow diagram is illustrated showing a method 300 for effectuating a healthcare plan including a plurality of clinical orders only upon receipt of an authorization from a first privileged clinician and a second privileged clinician with regard to at least one of the plurality of orders, in accordance with an embodiment of the present invention. As indicated at block 310, at the direction of a first privileged clinician, a healthcare plan is selected (e.g., from reference), or otherwise input, for a particular patient. The healthcare plan includes all order details necessary for each of the plurality of clinical orders to be effectuated and all appropriate clinical alerts for each of the plurality of clinical orders are provided. If any patient-specific order customizations are desired, such customizations are input, as indicated at block 312.

As indicated at block 314, the selected (or input) healthcare plan, including any customizations, is submitted and received, for instance, by the user input receiving component 218 of FIG. 2. Each of the plurality of orders included in the healthcare plan is validated, as indicated at block 316. In other words, it is determined (e.g., utilizing privilege verification component 220 of FIG. 2) whether review, authorization and/or verification from a second privileged clinician is necessary for any of the plurality of orders included in the healthcare plan to be effectuated.

With reference to FIG. 4, a screen display is shown of an exemplary user interface 400 for use, for instance, by a first privileged clinician, in inputting a clinical order requiring review by a second privileged clinician to be effectuated, in accordance with an embodiment of the present invention. In addition to areas for inputting and/or verifying various order details, the user interface 400 includes an "Additional Review Settings" display area. If it is determined that any of the phases within the healthcare plan (or orders within a healthcare phase) require review, authorization and/or verification by a second privileged clinician to be effectuated, the "Review Required" box is automatically checked. If desired, user action may override the automatic selection. Also included is a "Review Provider" box. In embodiments, the first privileged clinician is permitted to select a second privileged clinician, or group of privileged clinicians, for the subject order(s) to be routed to for review, authorization and/or verification. In embodiments, specification of a particular privileged clinician (or group of privileged clinicians) does not inhibit any clinician having appropriate ordering privileges from viewing and authorizing the subject order. Further, in embodiments, the "Review Provider" may have a default privileged clinician, or group of privileged clinicians, that displays in the "Review Provider" box. In still further embodiments, the "Review Provider" box may either be left blank or not be present at all. Any and all such variations, and any combination thereof, are contemplated to be within the scope of the present invention.

Figure 5:
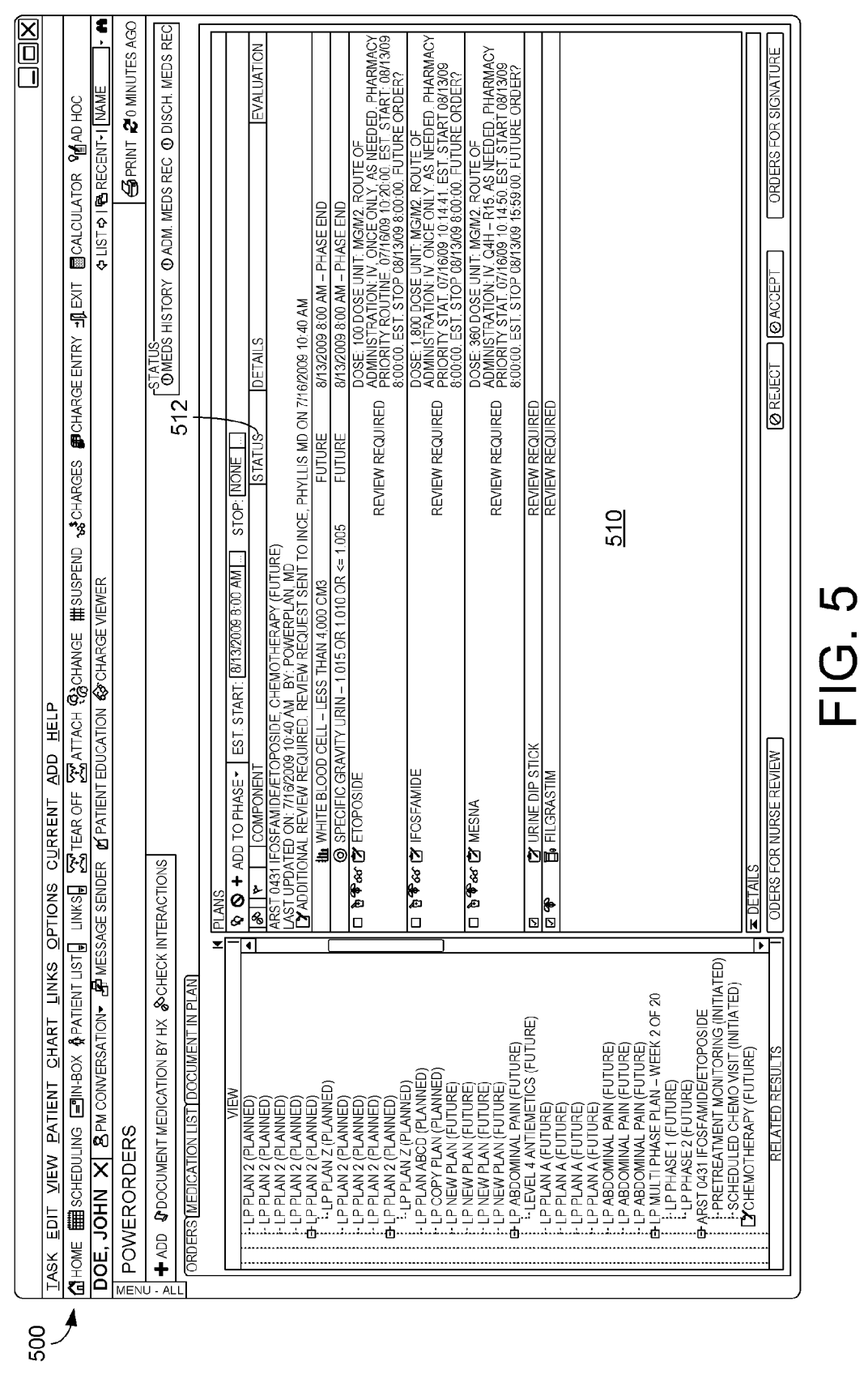

Returning to FIG. 3, upon determining that at least one of the plurality of orders included in the healthcare plan requires review by a second privileged clinician, each of the plurality of orders is assigned a non-effectuated (or "Review Required") status, e.g., by the status assigning component 222 of FIG. 2. This is indicated at block 318. With reference to FIG. 5, a screen display is illustrated showing an exemplary user interface 500 having orders that have been input by a first privileged clinician and require authorization by a second privileged clinician to be effectuated, such orders having a "Review Required" status, in accordance with an embodiment of the present invention. The user interface 500 includes an orders display area 510 that presents one or more clinical orders that have been received for a particular patient from a first privileged clinician. The user interface 500 further includes an order status display area 512 that presents a status indicator for each of the one or more orders. At least one of the status indicators indicates that review of the associated order is required by a second privileged clinician before the associated order can be effectuated. In the illustrated example, five orders have been received for the patient John Doe, each of the five orders being related to one another as part of a phase of a healthcare plan, and each of the five orders having a status indicator indicating that review, authorization and/or verification by a second privileged clinician is required for the order to be effectuated (i.e., have a status of "Review Required"). As more fully described below, due to the relationship between the five orders as part of a phase of a healthcare plan, if any one of the five orders is determined to require review, the status of all orders in the phase will be set to "Review Required."

Turning back to FIG. 3, a notification is generated (e.g., by the notification component 224 of FIG. 2) and routed to a second privileged clinician, the notification indicating that review and authorization of at least one of the orders in the healthcare plan is required before any of the plurality of orders can be effectuated. This is indicated at block 320. With reference to FIG. 6, a screen display is illustrated showing an exemplary user interface 600 in the form of a message center for notifying a second privileged clinician of orders requiring his or her review and authorization, in accordance with an embodiment of the present invention. In the "Inbox Summary" portion of the message center, an item titled "Protocol Review Orders" is shown as being selected, causing those clinical orders that have been routed to one or more privileged clinicians for review to be displayed. In the illustrated user interface 600, the clinical orders requiring review are organized by patient name. Upon selection of one of the patient names, the second privileged clinician may review the order(s) associated with this patient, as more fully described below with reference to FIG. 7.

With reference back to FIG. 3, the second privileged clinician then reviews the order(s) as required and either accepts or rejects the order(s), as indicated at block 322. As none of the orders in the healthcare plan are effectuated until any and all of the plurality of orders requiring review and authorization by a second privileged clinician are accepted, the entire healthcare plan is either accepted or rejected by the second privileged clinician. This is indicated at block 324. With reference to FIG. 7, a screen display is illustrated showing an exemplary user interface 700 having information with respect to orders requiring review that may be displayed upon selection of a particular patient name in the message center of FIG. 6, in accordance with an embodiment of the present invention. The information displayed in FIG. 7 is only that information which is determined to be relevant and significant to the reviewing privileged clinician. That is, the basic content of the orders in FIGS. 5 and 7 is the same but the level and content of the order detail differs. In FIG. 7, only details that are significant for the reviewing privileged clinician (e.g., dose, route, frequency, height, weight, BSA, and the like) are displayed. Also displayed and, in the illustrated example, highlighted so that they stand out more clearly, are any patient-specific exceptions that render the order unusual in any way. For instance, in the illustrated example, the parameters utilized to calculate dosages indicate a weight of 45 kg but the patient weight is 47 kg. This is relevant and significant information the reviewing privileged clinician is able to easily identify in the user interface 700 of FIG. 7, and review, before authorizing or rejecting an order. The second privileged clinician may review the displayed information and determine whether or not to accept or reject the order(s) requiring review.

Referring back to FIG. 3, if the second privileged clinician accepts the healthcare plan (that is, accepts those orders of the plurality that required review and acceptance/authorization), the healthcare plan is validated and a status of "effectuated" or "ordered" is assigned to each of the plurality of orders (e.g., utilizing status assigning component 222 of FIG. 2). This is indicated at block 326. Each of the plurality of orders is then released to those persons and/or departments from whom action is required for completion of the order, as indicated at block 328. With reference to FIG. 8, a screen display is illustrated showing an exemplary user interface 800 having orders that have been input by a first privileged clinician and received authorization by a second privileged clinician, such orders having an "Ordered" status, in accordance with an embodiment of the present invention.

If the second privileged clinician rejects the healthcare plan (that is, rejects one or more of the plurality of orders that requires review and acceptance/authorization), a notification is generated (e.g., utilizing notification component 224) and routed to the first privileged clinician. This is indicated at block 330. Upon rejection, the second privileged clinician has the ability to specify a reason for the rejection. Further, the second privileged clinician has the ability to specify which of a plurality of reviewed orders was the reason for the rejection. With reference to FIG. 11, a screen display is illustrated showing an exemplary user interface 1100 for use by a second privileged clinician to identify which order(s) among a plurality of orders related to one another as part of a healthcare plan or phase of a healthcare plan caused the second privileged clinician to reject the plan or phase and provide a reason for the rejection, in accordance with an embodiment of the present invention. As can be seen, one or more of the reviewed orders may be selected as requiring additional consideration (i.e., rejected). The second privileged provider may also either select from a drop-down box one of a plurality of delineated reasons for rejection and/or free-text a reason for rejection.

Figure 12:
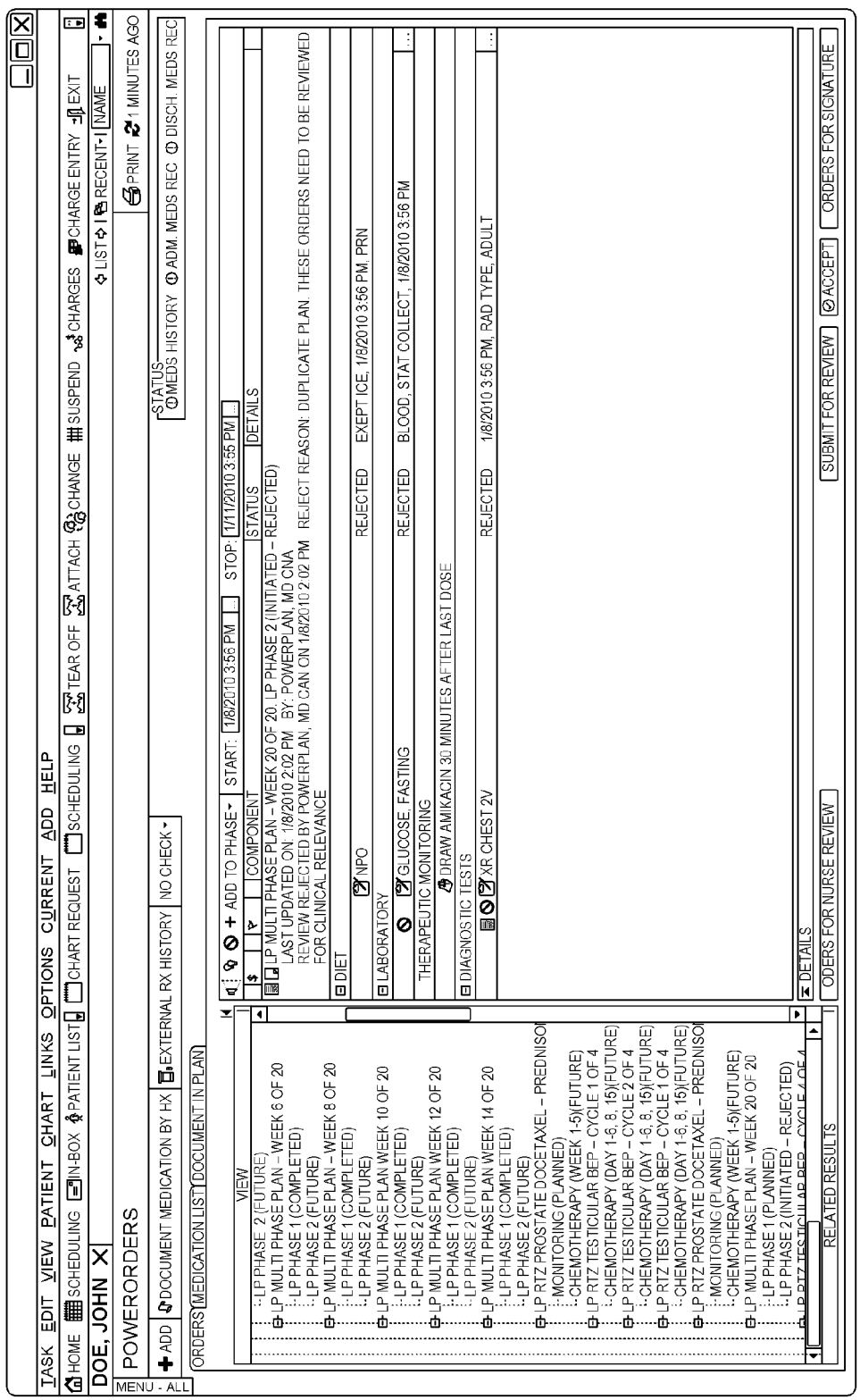
FIG. 12 is a screen display of an exemplary user interface illustrating that, once a second privileged clinician has rejected an order, the reason for the rejection may be displayed in a prominent location for further review by the first privileged clinician, in accordance with an embodiment of the present invention.

With reference to FIG. 12, an exemplary user interface 1200 in accordance with an embodiment of the present invention illustrates that, once a second privileged clinician has rejected an order, the reason for the rejection may be displayed in a prominent manner and/or location (e.g., in an healthcare plan or phase header, highlighted, bolded, italicized, presented in colored text, or the like) for further review by the first privileged clinician. Additionally, as shown in the exemplary user interface 1300 of FIG. 13, once a second privileged clinician has rejected an order, the reason for the rejection may be displayed in association with the healthcare plan information, in accordance with embodiments hereof.

Returning to FIG. 3, the first privileged clinician may then review the rejected orders, as indicated at block 332, make any necessary modifications and/or additional customizations, and submit the modified healthcare plan for review. As the status of all of the plurality of orders included in the healthcare plan remains non-effectuated (either "Pending Review" or "Rejected," as desired), the entire healthcare plan remains unexposed with respect to anyone other than those clinicians having appropriate ordering privileges.

Figure 9:
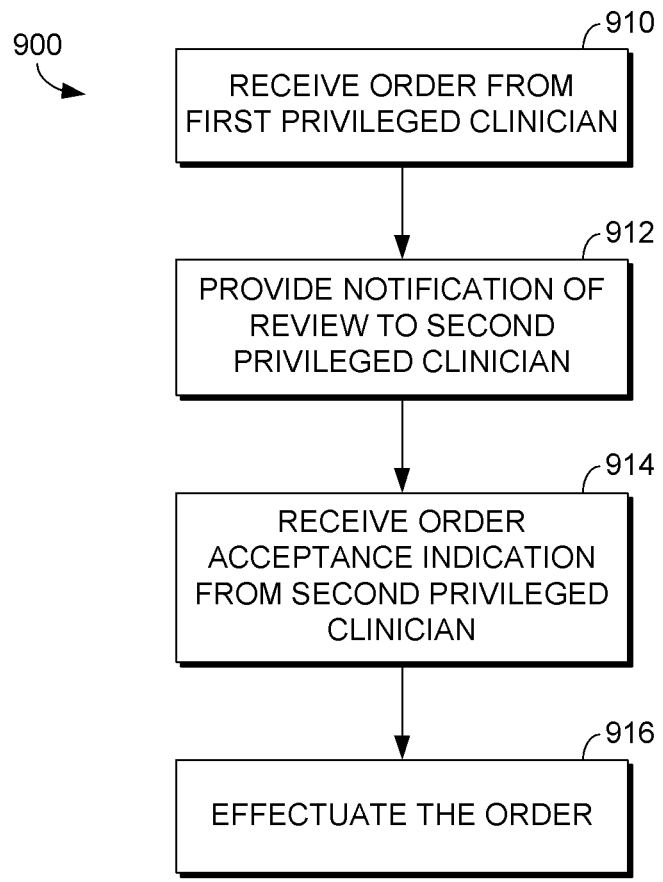
FIG. 9 is a flow diagram showing a method for effectuating clinical orders only upon receipt of an authorization from a first privileged clinician and a second privileged clinician, in accordance with an embodiment of the present invention.

With reference to FIG. 9, a flow diagram is illustrated showing a method 900 for effectuating clinical orders only upon receipt of an authorization from a first privileged clinician and a second privileged clinician, in accordance with an embodiment of the present invention. As indicated at block 910, an order (or a plan, phase of a plan, or the like) is received from a first privileged clinician (evidencing the first clinician's authorization of the order). The received order includes all order details necessary to effectuate the order and all appropriate clinical alerts related to the order are provided to the first privileged clinician at the time the order is input.

As indicated at block 912, a notification is provided to a second privileged clinician indicating that he or she must review and authorize the received order before the order can be effectuated. As indicated at block 914, once the second privileged clinician has reviewed and authorized the order, an order acceptance indication is received from the second privileged clinician, the order acceptance indication evidencing the second privileged clinician's authorization of the order. Unless the second privileged clinician modifies one or more order details associated with the order, at the time of review, the second privileged clinician is not provided any of the appropriate clinical alerts related to the order, as the first privileged clinician has already received such alerts and placed the order in accordance therewith.

Upon receipt of the order acceptance indication, the order is effectuated and, accordingly, exposed to those departments and/or individuals that are to take some action with respect to the order. This is indicated at block 916.

Figure 10:
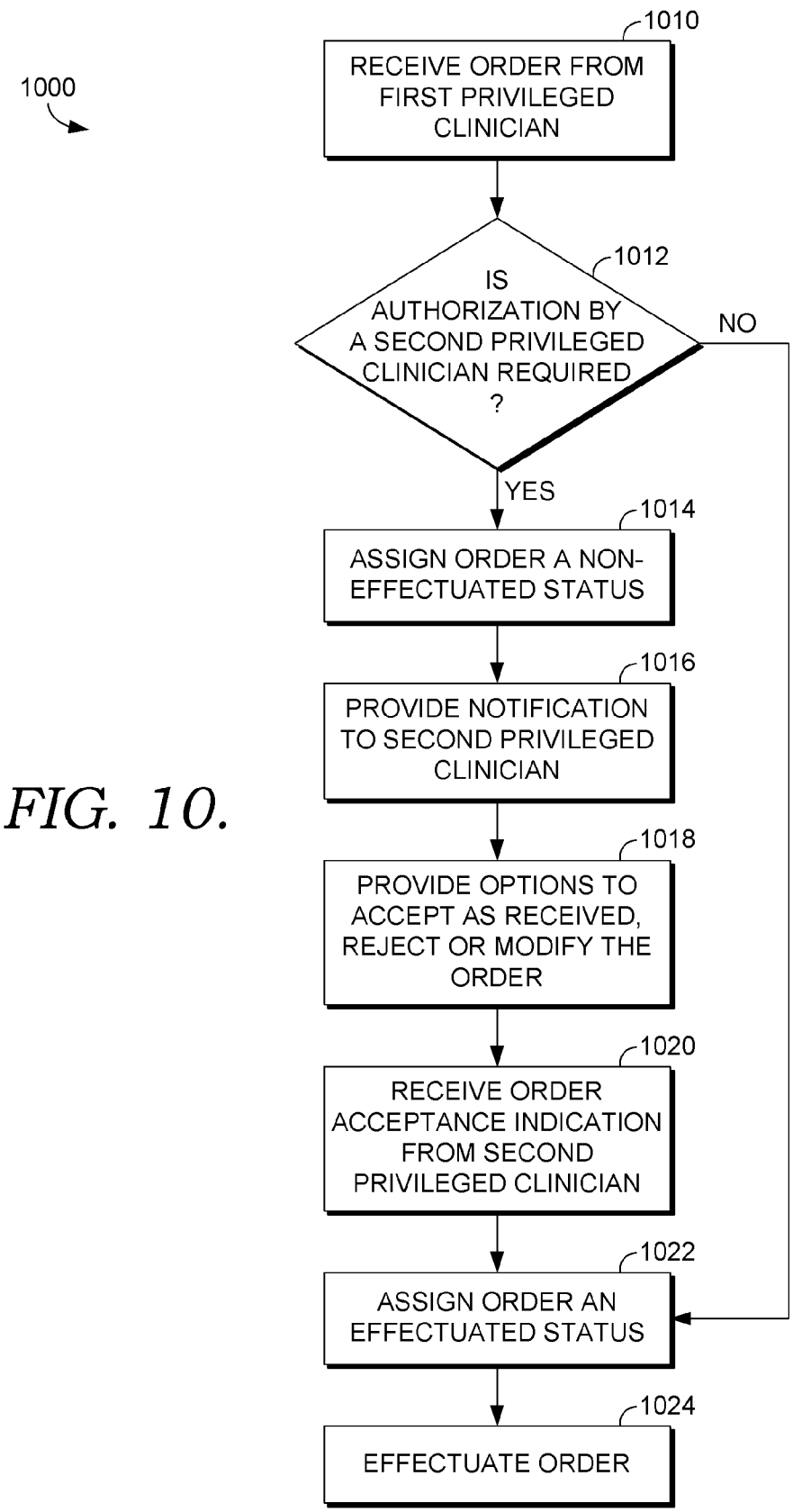
FIG. 10 is a flow diagram showing a method for effectuating clinical orders only upon receipt of an authorization from a first privileged clinician and a second privileged clinician, in accordance with an embodiment of the present invention.

With reference to FIG. 10, a flow diagram is illustrated showing a method 1000 for effectuating clinical orders only upon receipt of an authorization from a first privileged clinician and a second privileged clinician, in accordance with an embodiment of the present invention. As indicated at block 1010, an order (or a plan, phase of a plan, or the like) is received from a first privileged clinician (evidencing the first clinician's authorization of the order). The received order includes all order details necessary to effectuate the order and all appropriate clinical alerts related to the order are provided to the first privileged clinician at the time the order is input. In embodiments, the order may require action by one or more clinicians other than the first and second privileged clinicians. As indicated at block 1012, it is next determined whether review and authorization by a second privileged clinician is required for the order to be effectuated. If it is determined that review and authorization by a second privileged clinician is not required, the order is assigned an effectuated status, as indicated at block 1022, and the order is effectuated, as indicated at block 1024.

If, however, it is determined at block 1012 that review and authorization of the order by a second privileged clinician is required for the order to be effectuated, the order is assigned a non-effectuated status, as indicated at block 1014. While in the non-effectuated status, exposure of the order to clinicians that do not have appropriate ordering privileges to authorize the order is prevented—even if action by one or more such clinicians will be necessary once the order is effectuated.

As indicated at block 1016, a notification is provided to a second privileged clinician indicating that he or she must review and authorize the received order before the order can be effectuated. As indicated at block 1018, the second privileged clinician is provided the options of accepting the order as received, rejecting the order, or modifying the order and accepting the modified version thereof.

As indicated at block 1020, once the second privileged clinician has reviewed and authorized the order (either as is or in a modified form), an order acceptance indication is received from the second privileged clinician, the order acceptance indication evidencing the second privileged clinician's authorization of the order (or modified order, as appropriate). Upon receipt of the order acceptance indication, the status of the order is changed from "non-effectuated" to "effectuated," as indicated at block 1022, and the order is effectuated, as indicated at block 1024. One effectuated, the order exposed to those departments and/or individuals that are to take some action with respect to the order.

As can be understood, embodiments of the present invention provide computerized methods and systems in a clinical computing environment for effectuating clinical orders only upon receipt of an authorization from at least two privileged clinicians, that is, two clinicians having appropriate ordering privileges. Upon receipt of an order from a privileged clinician that requires authorization by at least two privileged clinicians, such order is assigned a non-effectuated status until such time as the required review by one or more other privileged clinicians is completed. While in the non-effectuated status, the order is not exposed to clinicians or others that do not have appropriate ordering privileges to prescribe and/or authorize the order.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more non-transitory computer-readable storage media having computer-executable instructions embodied thereon that, when executed, perform a method for effectuating clinical orders only upon receipt of an authorization from a first privileged clinician and a second privileged clinician, the method comprising:

receiving an order from the first privileged clinician, the received order including all order details necessary to effectuate the order;

providing a notification to the second privileged clinician, the notification indicating that review of the order by the second privileged clinician is required before the order can be effectuated, wherein each of the first privileged clinician and the second privileged clinician has ordering privileges;

receiving an order acceptance indication from the second privileged clinician; and upon receipt of the order acceptance indication, effectuating the order, wherein the order requires action by a clinician other than the first and the second clinicians, and wherein the order is exposed to the clinician only after the order acceptance indication is received, wherein receiving the order from the first privileged clinician comprises receiving a plurality of orders, each of the plurality of orders being associated with one another as part of a plan or a phase of a plan, wherein the method further comprises determining that at least one of the plurality of orders requires authorization of two privileged clinicians,
wherein the notification indicating that review of the order by the second privileged clinician is required indicates that review of the at least one of the plurality of orders is required,
wherein the order acceptance indication from the second privileged clinician indicates that the at least one of the plurality of orders is accepted, and
wherein upon receipt of the order acceptance indication, each of the plurality of orders is effectuated.

2. The one or more non-transitory computer-readable storage media of claim 1, wherein receipt of the order from the first privileged clinician evidences the first privileged clinician's authorization, and wherein receipt of the order acceptance indication from the second privileged clinician evidences the second privileged clinician's authorization.

3. The one or more non-transitory computer-readable storage media of claim 1, wherein all appropriate clinical alerts related to the order are provided to the first privileged clinician prior to providing the notification to the second privileged clinician.

4. The one or more non-transitory computer-readable storage media of claim 1, wherein the second privileged clinician comprises a plurality of privileged clinicians, and wherein each of the plurality of privileged clinicians has any privileges necessary to effectuate the order.

5. The one or more non-transitory computer-readable storage media of claim 1, wherein the received order includes at least one customization relative to a reference order.

6. One or more non-transitory computer-readable storage media having computer-executable instructions embodied thereon that, when executed, perform a method for effectuating clinical orders only upon receipt of an authorization from a first privileged clinician and a second privileged clinician, the method comprising:
receiving an order from the first privileged clinician, wherein the received order includes all order details necessary to effectuate the order, and wherein the order requires action by a third clinician other than the first and the second clinicians;
determining that the order requires authorization from the second privileged clinician to be effectuated, wherein each of the first privileged clinician and the second privileged clinician has ordering privileges;
assigning the order a non-effectuated status pending receipt of the authorization from the second privileged clinician, wherein the non-effectuated status prevents exposure of the order to the third clinician;
providing a notification to the second privileged clinician, the notification indicating that authorization of the order by the second privileged clinician is required before the order can be effectuated; and
providing the second privileged clinician with options to accept the order as received, reject the order, or accept a modified version of the order,
wherein receiving the order from the first privileged clinician comprises receiving a plurality of orders, each of the plurality of orders being associated with one another as part of a plan or a phase of a plan,
wherein determining that the order requires authorization from the second privileged clinician to be effectuated comprises determining that at least a first of the plurality of orders requires authorization of two privileged clinicians,
wherein at least a second of the plurality of orders requires action by the third clinician, and wherein the non-effectuated status prevents exposure of any of the plurality of orders to the third clinician.

7. The one or more non-transitory computer-readable storage media of claim 6, wherein the method further comprises:
receiving an order acceptance indication from the second privileged clinician indicating acceptance of the order as received, the received order acceptance indication evidencing the second clinician's authorization of the order; and
upon receipt of the order acceptance indication, assigning the order an effectuated status, wherein the effectuated status permits exposure of the order to the third clinician.

8. The one or more non-transitory computer-readable storage media of claim 6, wherein the method further comprises:
receiving an order acceptance indication from the second privileged clinician indicating acceptance of the modified version of the order, the received order acceptance indication evidencing the second clinician's authorization of the order; and
upon receipt of the order acceptance indication, assigning the order an effectuated status, wherein the effectuated status permits exposure of the order to the third clinician.

9. The one or more non-transitory computer-readable storage media of claim 6, wherein all appropriate clinical alerts related to the order are provided to the first privileged clinician prior to providing the notification to the second privileged clinician.

10. The one or more non-transitory computer-readable storage media of claim 6, wherein the second privileged clinician comprises a plurality of privileged clinicians, and wherein each of the plurality of privileged clinicians has any privileges necessary to effectuate the order.

11. The one or more non-transitory computer-readable storage media of claim 6,
wherein the notification indicating that review of the order by the second privileged clinician is required indicates that review of at least the first of the plurality of orders is required,
wherein the method further comprises receiving an order acceptance indication from the second privileged clinician, the order acceptance indication indicating that at least the first of the plurality of orders is accepted, and
wherein upon receipt of the order acceptance indication, each of the plurality of orders is effectuated.

12. The one or more non-transitory computer-readable storage media of claim 6, wherein the first and the second of the plurality of orders are the same order.

13. The one or more non-transitory computer-readable storage media of claim 6, wherein the first and the second of the plurality of orders are different orders.

14. One or more non-transitory computer-readable storage media having computer-executable instructions embodied thereon that, when executed, cause presentation of a user interface, the user interface comprising:
an orders display area that presents one or more orders that have been received for a particular patient from a first privileged clinician; and
an order status display area that presents a status indicator for each of the one or more orders, at least one of the status indicators indicating that review of an associated order is required by a second privileged clinician before the associated order can be effectuated, wherein each of the first privileged clinician and the second privileged clinician has ordering privileges, wherein the associated order includes all order details necessary to effectuate the order;

wherein upon receiving an order acceptance indication from the second privileged clinician the associated order is effectuated, wherein the associated order requires action by a clinician other than the first and the second clinicians, and wherein the associated order is exposed to the clinician only after the order acceptance indication is received, wherein receiving the associated order from the first privileged clinician comprises a plurality of orders, each of the plurality of orders being associated with one another as part of a plan or a phase of a plan, wherein at least one of the plurality of orders requires authorization of two privileged clinicians, wherein the notification indicating that review of the order by the second privileged clinician is required indicates that review of the at least one of the plurality of orders is required, wherein the order acceptance indication from the second privileged clinician indicates that the at least one of the plurality of orders is accepted, and wherein upon receipt of the order acceptance indication, each of the plurality of orders is effectuated.

15. The one or more non-transitory computer-readable storage media of claim 14, wherein the at least one of the status indicators changes to indicate that the associated order is effectuated upon receipt of an acceptance indicator from the second privileged clinician.

* * * * *